United States Patent
Iwata et al.

(10) Patent No.: US 8,137,623 B2
(45) Date of Patent: Mar. 20, 2012

(54) TASTE ANALYZING APPARATUS

(75) Inventors: Yosuke Iwata, Kyoto (JP); Tsuyoshi Kobayashi, Kanagawa (JP)

(73) Assignees: Shimadzu Corporation, Kyoto (JP); Takasago International Corporation, Tokyo (JP)

( * ) Notice: Subject to any disclaimer, the term of this patent is extended or adjusted under 35 U.S.C. 154(b) by 497 days.

(21) Appl. No.: 11/808,046

(22) Filed: Jun. 6, 2007

(65) Prior Publication Data

US 2007/0288117 A1 Dec. 13, 2007

(30) Foreign Application Priority Data

Jun. 7, 2006 (JP) .................................. 2006-158037

(51) Int. Cl.
*G01N 15/06* (2006.01)
(52) U.S. Cl. ............. 422/68.1; 422/50; 422/69; 422/82; 436/52; 436/53
(58) Field of Classification Search ...................... 99/275; 422/68.1, 50, 69, 81, 82, 82.01–82.03, 99–104; 436/43, 52, 53, 63, 174, 178, 180; 73/1.01, 73/1.02, 53.01
See application file for complete search history.

(56) References Cited

U.S. PATENT DOCUMENTS

| | | | | |
|---|---|---|---|---|
| 3,695,897 A * | 10/1972 | Uchida | ........................ | 426/429 |
| 5,221,521 A * | 6/1993 | Hashizume et al. | ........... | 422/100 |
| 5,603,899 A * | 2/1997 | Franciskovich et al. | ...... | 422/100 |
| 5,783,450 A * | 7/1998 | Yoshida et al. | ................ | 436/161 |
| 6,489,132 B1 * | 12/2002 | Gordon et al. | ............... | 435/7.92 |
| 7,066,011 B2 * | 6/2006 | Yamauchi et al. | ........... | 73/61.59 |
| 2003/0013198 A1 * | 1/2003 | Harada | ........................... | 436/20 |
| 2004/0124128 A1 * | 7/2004 | Iwata | ......................... | 210/198.2 |

FOREIGN PATENT DOCUMENTS

JP 62-187252 A 8/1987
JP 01-274062 A 11/1989
(Continued)

OTHER PUBLICATIONS

"Products, Taste Sensing System: SA402B", [online], Intelligent Sensor Technology, Inc., [Search Date: Mar. 19, 2007], Internet http://www.insent.co.jp/english/Products.htm.

(Continued)

*Primary Examiner* — Henry Yuen
*Assistant Examiner* — Jianying Atkisson
(74) *Attorney, Agent, or Firm* — Westerman, Hattori, Daniels & Adrian, LLP

(57) ABSTRACT

The present invention provides an apparatus for analyzing easily not only the overall taste of a sample but also what kind of components, synergetic effects and diminishing effects contribute to the taste. A sample to be analyzed is injected into a mobile phase by a liquid sending pump, and the sample is sent to a taste detector by way of a blending means and valves. Then, detection signals are obtained by taste sensors on the taste detector. The sample sent through the taste detector is introduced into a column by way of a 6-port-2-position valve, temporally separated into components and eluted from the column. After each component is detected by a UV detector, the eluted liquid is sent to the taste detector once more, and detection signals which reflect the tastes of each sample component. When analyzing how the taste changes by an additive, send the additive to the blending means and blend it with the sample.

8 Claims, 5 Drawing Sheets

FOREIGN PATENT DOCUMENTS

| | | |
|---|---|---|
| JP | 03-067562 A | 3/1991 |
| JP | 03-163351 A | 7/1991 |
| JP | 04-324351 A | 11/1992 |
| JP | 06-174689 A | 6/1994 |
| JP | 07-021488 B2 | 3/1995 |
| JP | 07-103934 A | 4/1995 |
| JP | 08-271473 A | 10/1996 |
| JP | 08-285813 A | 11/1996 |
| JP | 08-306530 A | 11/1996 |
| JP | 10-253583 A | 9/1998 |
| JP | 10-267894 A | 10/1998 |
| JP | 2000-171423 A | 6/2000 |
| JP | 2000-283953 A | 10/2000 |
| JP | 2000-283955 A | 10/2000 |
| JP | 2000-283956 A | 10/2000 |
| JP | 2001-264289 A | 9/2001 |
| JP | 2002-243695 A | 8/2002 |
| JP | 3390194 B2 | 3/2003 |
| JP | 3632710 B2 | 3/2005 |
| WO | WO 02101381 A1 * | 12/2002 |

OTHER PUBLICATIONS

"Kansei Biosensor To It Shakai", IEEJ Transactions on Sensors and Micromachines, vol. 124, No. 7, 2004, pp. 229-232.

Chinese Office Action dated Dec. 4, 2009 (mailing date), issued in corresponding Chinese Patent Application No. 200710108251.1.

Chinese Office Action dated Jan. 25, 2011, issued in corresponding Chinese Patent Application No. 200710108251.1.

Japanese Office Action dated Jan. 18, 2011, issued in corresponding Japanese Patent Application No. 2006-158037.

Islam, A.K.M. Shafiqul et al.; "Taste Profiling of Centella Asiatica by a Taste Sensor"; Sensors and Materials, 2003, vol. 15, No. 4, pp. 209-218.

Chinese Office Action dated Aug. 16, 2011, issued in corresponding Chinese Patent Application No. 200710108251.1.

* cited by examiner

TASTE ANALYZING APPARATUS

The present invention relates to a taste analyzing apparatus for analyzing the tastes of foods or drinks, as a substitute or supplement for the human sense of taste.

BACKGROUND OF THE INVENTION

Conventionally, taste determination and taste evaluation of beverages, foods, and oral drugs are carried out by sensory evaluation methods using human gustatory sensation. In Taste Dilution Analysis, which is one of such sensory evaluation methods, a plurality of subjects (or panelists) evaluate the taste of a sample to be analyzed by diluting the sample in small steps, and determine the last remaining taste after a significant diluting step. However, since the evaluations vary between panelists and vary due to the panelist's daily physical condition and emotional feelings, it may be difficult to obtain objective and reproducible evaluations even if the test is carried out by more than one panelist. In addition, it is difficult to ensure or foster panelists because a panelist is required to take constant control of his/her own health care.

Meanwhile, it is essential to evaluate tastes when developing food or drink products or when practicing quality control of a manufacturing line. Therefore, an apparatus comparable to the human sense of taste which can evaluate taste is earnestly desired. At the same time, such taste sensing systems as disclosed in Patent Document 1 and Non-Patent Document 1 for example are conventionally known. It is known that an interaction between the lipid membrane (polymer membrane) and a chemical substance to be analyzed causes potential difference changes between a lipid membrane electrode and a standard reference electrode. Using this potential difference, such taste sensing systems evaluate the taste of a sample to be analyzed.

Specifically, the system disclosed in Patent Document 1 comprises eight taste sensors which measure potential differences using plural lipid membranes, and analyze the tastes by performing a principal component analysis or multiple linear regression analysis of the detection output from each sensor. At present, five tastes, namely, saltiness, sourness, umami (savoriness), bitterness, and astringency can be analyzed in practical use. The eight taste sensors are divided into two sensor groups of four sensors according to their characteristics.

The system proceeds an analysis in line with the following steps:
(1) Bring the taste sensors belonging to each sensor group into contact with a reference solution in a container which is the basis of the signal outputs, and wait until the signal output from each taste sensor is stabilized.
(2) Bring the taste sensors belonging to each sensor group into contact with a liquid sample to be analyzed in a container, and monitor the changes of each signal output.
(3) Run a principal component analysis (or multiple linear regression analysis) program to the monitored signals and determine the taste.
(4) Once again bring the taste sensors belonging to each sensor group into contact with a reference solution in a container, wait until the signal output from the taste sensors are stabilized, and confirm that the signal level returns to the level before monitoring (i.e. the signal level in step (1)).
(5) If, in step (4), the signal level does not return to the level before monitoring, cleanse each taste sensor with cleaning fluid.

Such a conventional taste sensing system is designed to evaluate the comprehensive taste or tastes of a whole sample to be analyzed, and a variety of test results are made public. However, since such previous taste sensing systems cannot capture individual tastes of various substances included in a sample, it is not possible to study what kind of substance contributes to the overall taste of the sample, or investigate the relationship between the combination of the taste of each substance and the overall taste.

In addition, a condition being that, when plural tastes are mixed, a certain taste changes in the human sense or inversely does not change in the human sense but causes change of a measurement value is conventionally known. Quinine, for example, known as an antimalarial drug, has an intense bitter taste, but if a sweet component such as sucrose is added to it, the measured bitter taste value is reduced although the bitter taste is not reduced in the human sense (see Non-Patent Document 2). Like this example, when studying how the taste changes depending on the presence or absence of an additive with the conventional taste sensing system, unfortunately it takes much time and effort to analyze: it is required to prepare both a sample with an additive and a sample without an additive, and then perform the analyses independently.

[Patent Document 1] Japanese Unexamined Patent Application Publication No. H3-163351

[Non-Patent Document 1] "Products, Taste Sensing System : SA402B", which is disclosed in the Website of Intelligent Sensor Technology, Inc.

[Non-Patent Document 2] "KANSEI BIOSENSOR TO IT SHAKAI", IEEJ Transactions on Sensors and Micromachines, Vol. 124, No. 7, 2004, pp. 229-232.

To solve the above-described problem, the present invention intends to provide a taste analyzing apparatus for obtaining detailed knowledge such as a relationship between the overall taste of a sample and the taste of each of the various components contained in the sample, by measuring the individual taste of the various components contained in the sample minutely and objectively.

SUMMARY OF THE INVENTION

Thus, an aspect in accordance with the present invention provides a taste analyzing apparatus for analyzing tastes which a liquid sample has, comprising:

a) a component separator for temporally separating components contained in a liquid sample to be analyzed;

b) a first detector including a plurality of taste sensors, each of which has a different responsive property, for detecting the components in the liquid sample separated by the component separator in temporal course; and c) a signal processor for obtaining information on a taste corresponding to each component of the sample by processing detection signals obtained by the plurality of taste sensors.

Preferably, it is possible to use a separation column of a liquid chromatograph (LC) as the component separator.

According to the taste analyzing apparatus set forth in the aspect of the present invention, a liquid sample to be analyzed is temporally separated with a separation column of an LC, for example, and then the eluted liquid containing each separated sample component is introduced into the first detector. In the first detector, the introduced eluted liquid touches plural taste sensors, and the sensors produce detection signals according to the sample components in the eluted liquid. When the introduced sample components change as time proceeds, the detection signals also change. Hence the signal processor calculates information on the taste, e.g. quality of taste, corresponding to each sample component based on each detection signal which fluctuates as time proceeds. Therefore, it is possible to determine minutely not the overall taste of the sample but each taste of various components contained in the sample.

In accordance with the invention, it is preferable to put the liquid sample after separated into components by the component separator through a flow cell detector, i.e. the first detector, and then introduce the sample into a detecting element such as a visible-ultraviolet spectrophotometer or mass spectrometer. Or, it is also preferable to put the liquid sample after separated into components by the component separator through a detecting element such as a visible-ultraviolet spectrophotometer with a flow cell and then introduce the sample into the first detector. By determining the quantity and/or quality of each sample component based on the detection signal obtained by the detecting element, it is possible to relate the kind, contained amount, and taste of each sample component contained in the liquid sample, and then display or print the result. Therefore, it is possible to obtain information on various components contained in the sample and information on the taste of each of the components (e.g. quality of taste) clearly and individually.

Preferably, the taste analyzing apparatus set forth in the aspect of the present invention may further comprise a second detector including a plurality of taste sensors, each of the taste sensors having a different responsive property, for detecting tastes of the liquid sample before being separated into components by the component separator.

In this case, the first detector and the second detector may be independent. However, considering the costs and a variation in detection due to the individual difference of each taste sensor, it is preferable that the first detector and the second detector be one detector, and that the taste analyzing apparatus further comprise a passage switcher for selectively supplying the liquid sample before being separated into components by the component separator or a liquid eluted from the component separator to the detector.

Since both the overall taste of a sample and the taste of each of the various components contained in the sample are obtained in a single analysis, information such as the degree of contribution of the taste of each component to the overall taste of the sample, or relationship between the overall taste of the sample and the taste of each component is obtained easily and effectively.

Preferably, the taste analyzing apparatus set forth in the aspect of the present invention may further comprise an additive blender for selectively blending an additive into the sample before and/or after being separated into components by the component separator, wherein the sample separated into components by the component separator, each of the components being blended with the additive, is detected and/or the sample being blended with the additive but not having been separated yet is detected.

In this case, it is possible to analyze easily and automatically, for example, how taste changes when an additive which has a synergetic effect or diminishing effect on the taste of a sample is or is not added.

Also preferably, the taste analyzing apparatus set forth in the aspect of the present invention may further comprise a diluter for diluting the liquid sample, and the liquid sample properly diluted is detected before and/or after separated into components.

In this case, it is possible to automatically perform an evaluation equivalent to the Taste Dilution Analysis by decreasing in steps the concentration of the liquid sample by the diluter and analyzing the taste of the whole sample or the taste of each sample component in each of the stages.

EXPLANATION OF NUMERALS 10a, 10b, 10c, 15a, 15b, 15c . . . Container
11 . . . First Switching Valve
12 . . . First Liquid Sending Pump
13 . . . Autosampler
14 . . . First 6-Port-2-Position Valve
23 . . . Second 6-Port-2-Position Valve
16 . . . Second Switching Valve
17 . . . Second Liquid Sending Pump
18, 22 . . . 7-Port-6-Position Valve
19 . . . Column
20 . . . UV Detector
21 . . . Blending Means
30 . . . Taste Detector
31 . . . Flow Sensor
32 . . . Sensor Block
33 . . . Lipid/Polymer Membrane
34 . . . Electrodes
35 . . . Plug
36 . . . Flow Passage Block
37 . . . Reference Electrode
40 . . . Signal Processing Means

DETAILED DESCRIPTION OF PREFERRED EMBODIMENTS (First Embodiment)

Figure 1:
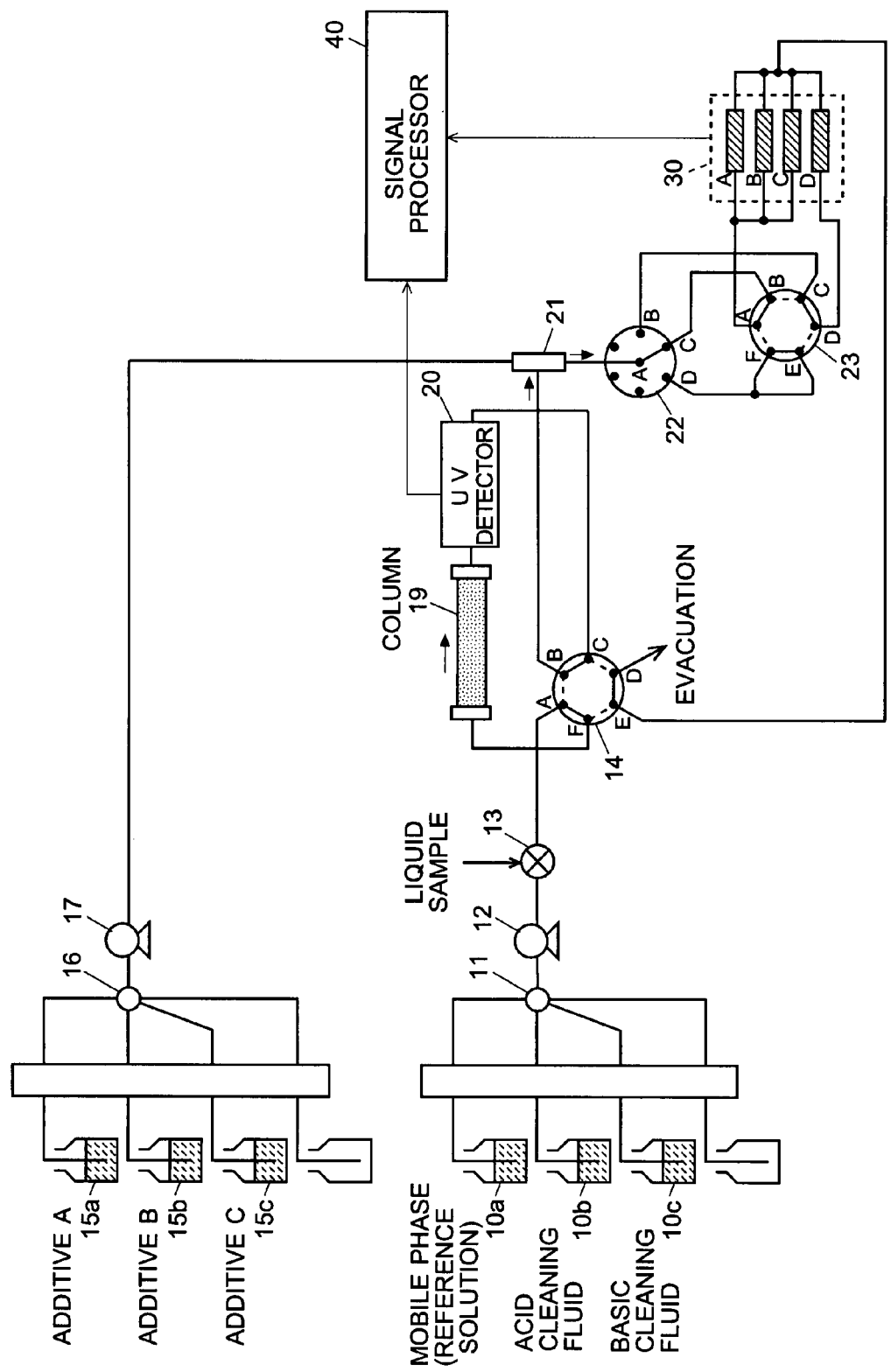
FIG. 1 is a schematic diagram showing the passages of the taste analyzing apparatus according to an embodiment of the present invention.

A first embodiment of the taste analyzing apparatus in accordance with the present invention is described with reference to the drawings. FIG. 1 is a schematic diagram showing the passages of the taste analyzing apparatus of this embodiment.

In this embodiment, a container 10a contains mobile phase (reference solution), a container 10b contains acid cleaning fluid, and a container 10c contains basic cleaning fluid. One of the containers 10a, 10b, or 10c, is selected by a first switching valve 11, and the fluid contained in the selected container is sent to a port A of a first 6-port-2-position valve 14 through an autosampler 13 by a first liquid sending pump 12. A container 15a contains an additive A, a container 15b contains an additive B, and a container 15c contains an additive C. The additives A, B, and C are different. When a second liquid sending pump 17 is activated, one of the additives A, B, or C selected by a second switching valve 16 is sent to an inlet port of a blending means 21.

Both the first 6-port-2-position valve 14 and a second 6-port-2-position valve 23 which will be explained later, can be switched to either one of two states depending on how two adjacent ports are linked: a state as shown by solid lines or a state as shown by broken lines in FIG. 1. Between a port F and C of the first 6-port-2-position valve 14, a column 19 for a size exclusion chromatography as the component separator in accordance with a first embodiment of the present invention and a UV detector (a visible-ultraviolet spectrophotometer) 20 are placed. A port D is connected to an outlet. A port B is connected to another inlet port of the blending means 21. An outlet port of the blending means 21 is connected to a center port A of a 7-port-6-position valve 22. The 7-port-6-position valve 22 has six ports around one center port A, and one of the six ports is selectively connected to the center port A.

Port A and port B of the 7-port-6-position valve 22 are connected to a port B and port C of the second 6-port-2-position valve 23, respectively. A port D of the 7-port-6-position valve 22 is connected to both port E and port F of the second 6-port-2-position valve 23. Port A of the second 6-port-2-position valve 23 is connected to an inlet of a taste sensor A, taste sensor B, and taste sensor C included in a taste detector 30 which can be a common detector of the first detector and the second detector in accordance with a first embodiment of the present invention. Port D of the second 6-port-2-position valve 23 is connected to an inlet of taste sensor D of the taste detector 30. All outlet ports of taste sensors A, B, C, and D are connected to port E of the first 6-port-2-position valve 14. Each of the taste sensors A, B, C, and D corresponds to each of the sensor blocks, which are described later. The taste sensors A, B, and C are minus sensors, and the taste sensor D is a plus sensor.

A detection signal from the UV detector 20 and a detection signal from the taste detector 30 are input to a signal processing means 40 as the signal processor in accordance with a first embodiment of the present invention. The signal processing means 40 is configured on the basis of CPU or proprietary DSP, and includes a program for calculating information, which is described later, by processing the detection signals. The signal processing means 40 also has a controller for controlling valves 14, 22, 23 and pumps 12 and 17, for example.

Figure 2:
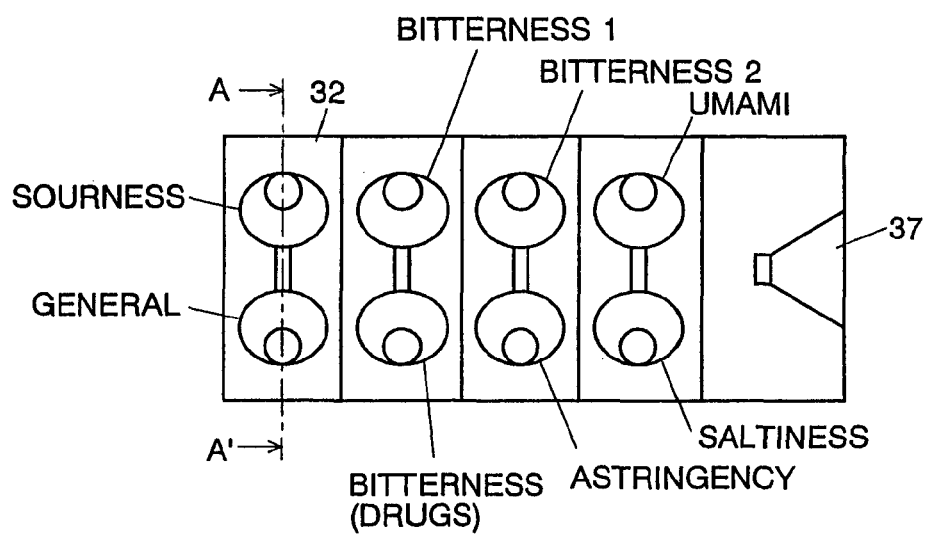
FIG. 2 is a schematic top view of a flow sensor in a taste detector.
Figure 3:
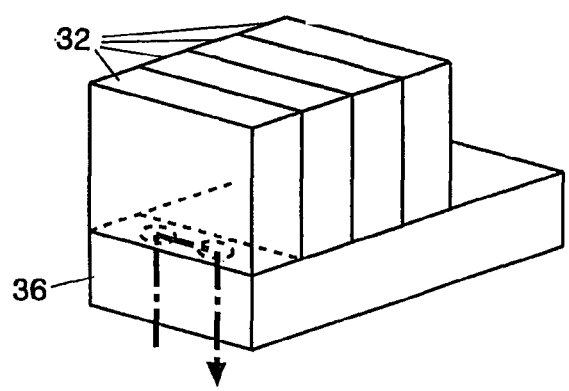
FIG. 3 is a schematic perspective view of a flow sensor in a taste detector.
Figure 4:
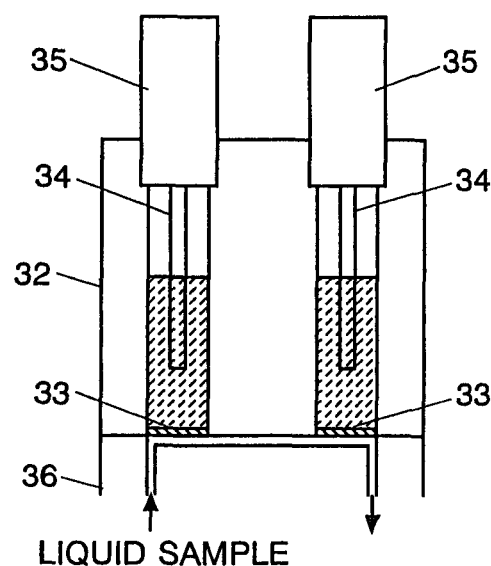
FIG. 4 is a cross sectional view of the flow sensor taken along the line A-A of FIG. 2.
Figure 5:
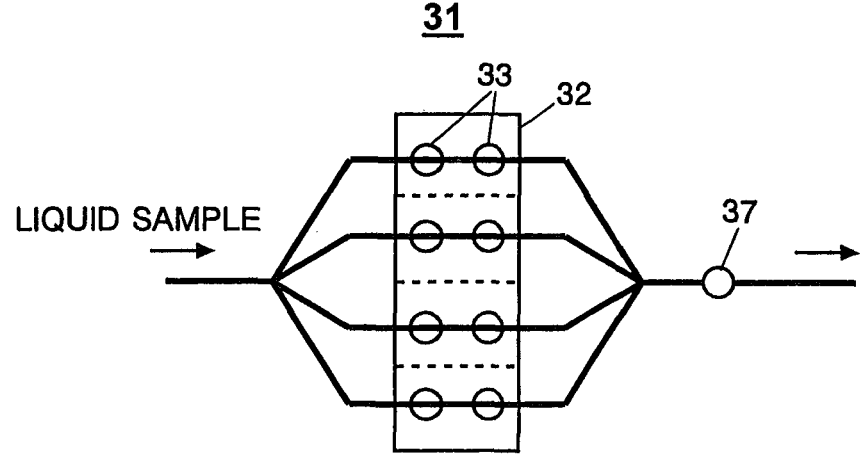
FIG. 5 is a flow passage diagram in a taste detector.

FIG. 2 through FIG. 5 are diagrams of a flow-type taste detector 30 in accordance with a first embodiment of the present invention. FIG. 2 is a schematic top view, FIG. 3 is a schematic perspective view of a flow sensor 31. FIG. 4 is a cross sectional view of the flow sensor 31 taken along the line A-A of FIG. 2. FIG. 5 is a flow passage diagram. The flow sensor 31 consists of sensor blocks 32, electrodes 34, a flow passage block 36, and a reference electrode 37. The sensor block 32 has two tubular electrolytic tanks inside, and a lipid/polymer membrane 33 is adhered to a bottom aperture of the electrolytic tank by vinyl chloride resin and tetrahydrofuran (THF). The electrode 34 is made of Ag, kept by plugs 35 and contained inside the sensor block 32. Inside the flow passage block 36 is a flow passage which leads a liquid sample to the lipid/polymer membranes 33.

Before measuring, a saturated silver chloride (AgCl) solution, which is an electrolytic solution, is injected inside the sensor block 32 to soak the lower portion of the electrode 34. When a liquid sample flows along the flow passage inside the flow passage block 36 and the liquid sample touches the lipid/polymer membrane 33, a potential response changes. The potential response is detected through the electrolytic solution by the electrodes 34 and the detection signal is sent to the signal processing means 40 as described earlier. Two kinds of lipid/polymer membrane 33 are adhered to each of the sensor blocks 32, and each lipid/polymer membrane 33 responds to different tastes. It should be noted that these two lipid/polymer membranes 33 which are adhered to one sensor block 32 should not interact with one another by eluted components from the membranes. Since the flow sensor 31 has four sensor blocks 32 and each of the sensor blocks 32 has two lipid/polymer membranes 33, it is possible to analyze eight kinds of taste in total. In this embodiment, as shown in FIG. 2, the following tastes are analyzed: sourness, umami, astringency, saltiness, three kinds of bitterness, and general which is not specified to any taste.

The liquid sample (mobile phase) flown through an inflow gate branches into four passages. These four liquid samples touch the lipid/polymer membranes 33 of each of the sensor blocks 32, converge, and then flow out through the common reference electrode 37. Since the flow passages according to each sensor block 32 converge at the entrance side and the exit side, when the flow of the mobile phase is stopped, a liquid sample containing components eluted from a membrane in one sensor block 32 may naturally diffuse into another sensor block 32 to intrude into a membrane in the sensor block. In order to avoid contamination between the membranes, it is necessary to supply continuously or at least without absence a mobile phase for carrying the sample, or place check valves at both the entrance side and the exit side of the flow passage of each sensor block 32.

An operation of a taste analyzing apparatus comprising the above-described elements will now be described. The first 6-port-2-position valve 14 is set to the state shown by broken lines in FIG. 1. The second 6-port-2-position valve 23 is set to the state shown by solid lines in FIG. 1. The 7-port-6-position valve 22 is set to connect ports A and D. Then, a mobile phase which is selected by the first switching valve 11 is sucked and sent to the autosampler 13 by the first liquid sending pump 12. As a mobile phase, 10 mM KCl or 10 mM KCl+0.3 mL tartaric acid aqueous solution, for example, are preferable. The preferable flow rate is, for example, 1 mL/min.

A liquid sample is injected into the mobile phase at a predetermined timing by the autosampler 13, and the liquid sample is sent to the blending means 21 by way of the first 6-port-2-position valve 14. If the second liquid sending pump 17 is not activated, the liquid sample flows directly thorough the blending means 21, thorough ports A and D of the 7-port-6-position valve 22, through ports E, F, A, and D of the second 6-port-2-position valve 23, and finally reaches the taste detector 30. While the liquid sample flows through the taste detector 30, detection signals are obtained by each of the taste sensors A through D. The detection signals are sent to the signal processing means 40.

The liquid samples that flew through each of the taste sensors in the taste detector 30 converge and flow to port E of the first 6-port-2-position valve 14. Then the liquid sample flows out from port F of the first 6-port-2-position valve 14 to the column 19. While flowing thorough the column 19, various components contained in the liquid sample are separated in accordance with their molecular weights and elute in the order of time from the outlet. The eluted liquid is introduced into the UV detector 20, and various components in the eluted liquid are detected in series as time proceeds; that is, signals which show the absorbance of light of the wavelength in accordance with the kind of sample component included in the eluted liquid are obtained in series. The obtained signals are sent to the signal processing means 40.

At the timing immediately after the liquid sample is introduced into the column 19, the connection state of the first 6-port-2-position valve 14 is switched from the state shown by broken lines in FIG. 1 to that shown by solid lines in FIG. 1. Consequently, the eluted liquid which flew through the UV detector 20 is sent to the blending means 21 by way of ports C and B of the first 6-port-2-position valve 14. As previously described, if the second liquid sending pump 17 is not activated, the eluted liquid flows through the blending means 21 and is introduced again into the taste detector 30. Since the liquid sample injected by the autosampler 13 is now separated into components by the column 19, a plurality of sample components are introduced into the taste detector 30 as time proceeds. Subsequently, detection signals according to each of the sample components can be obtained by taste sensors A to D. The eluted liquid which flew through the taste detector 30 flows back to port E of the first 6-port-2-position valve 14, and is evacuated from port D.

As the liquid sample and the eluted liquid which is obtained by separating the liquid sample into components flow, the following three detection signals are sent to the signal processing means 40: (1) the detection signal of the liquid sample before separated, detected by the taste detector 30, (2) the detection signal of the eluted liquid which contains various temporally-separated components, detected by the taste detector 30, (3) the detection signal of the eluted liquid which contains various temporally-separated components, detected by the UV detector 20. The signal processing means 40 performs predetermined arithmetic processing of each of the detection signals to obtain information on the sample to be analyzed.

Specifically, the signal processing means 40 obtains information on the overall taste by performing principal component analysis, multiple linear regression analysis, or other applicable multivariable analyses of detection signals of the liquid sample before being separated into components detected by the taste detector 30. In addition, the signal processing means 40 produces chromatograms at wavelengths based on detection signals, which are obtained by the UV detector 20, of the eluted liquid containing various temporally-separated sample components, detects peaks on these chromatograms, and performs qualitative analysis of the detected peaks to identify each of the sample components and deduces each contained amount. Furthermore, the signal processing means 40 extracts detection signals detected by the taste detector 30 at the timing when each of the identified various components is introduced into the taste detector 30, and performs principal component analysis, multiple linear regression analysis, or other applicable multivariable analyses of the extracted detection signals to obtain information on the taste of each of the various components contained in the sample. Using these results, therefore, it is possible, for example, to analyze the relationship between the kinds, quantities, and tastes of each of the components contained in the sample to be analyzed and the overall taste of the whole sample in which these sample components are blended.

With the taste analyzing apparatus according to an embodiment of the present invention, it is possible to perform another type of analysis in addition to the standard analysis as previously described. For example, it is possible to examine how the taste of the sample changes by the addition of an additive in such a mode as follows.

In this mode, basically, an analysis of a liquid sample is performed using such flow passages as explained earlier. For example, an additive selected by the second switching valve 16 is sent to the blending means 21 by activating the second liquid sending pump 17 at a predetermined timing after the liquid sample is injected. Consequently, the additive is blended by the blending means 21 with the liquid sample before separated into components which flew thorough ports A and B of the first 6-port-2-position valve 14, and is sent to the taste detector 30 as previously described. Specifically, the containers 15a through 15c, the second switching valve 16, the second liquid sending pump 17, and the blending means 21 function as the additive blender in accordance with an embodiment of the present invention.

Accordingly, in this mode, it is possible to obtain the taste of a sample which is influenced by an additive. Since no additives are injected while the second liquid sending pump 17 is not activated as stated earlier, it is possible to easily select whether an additive is blended or not with the liquid sample which is introduced into the taste detector 30 by controlling only the second liquid sending pump 17. Hence, the change of the taste by the addition of an additive can be measured simply and easily. Specifically, by flowing 10 mM KCl+0.3 mL tartaric acid aqueous solution as a mobile phase at the flow rate of 1 mL/min, using quinine as a sample to be analyzed, adding sucrose as an additive, it is possible to confirm that the bitterness of quinine is reduced by the effect of the sucrose.

In addition, by activating the second liquid sending pump 17 at the timing when the sample separated into components by flowing through the column 19 flows through the blending means 21, it is possible to blend the additive selected by the second switching valve 16 with each of the separated components. Hence, by measuring the change of the taste of the combination of each component and an additive, it is possible to find out components which contribute to the taste change and the degree of the contribution.

Figure 7:
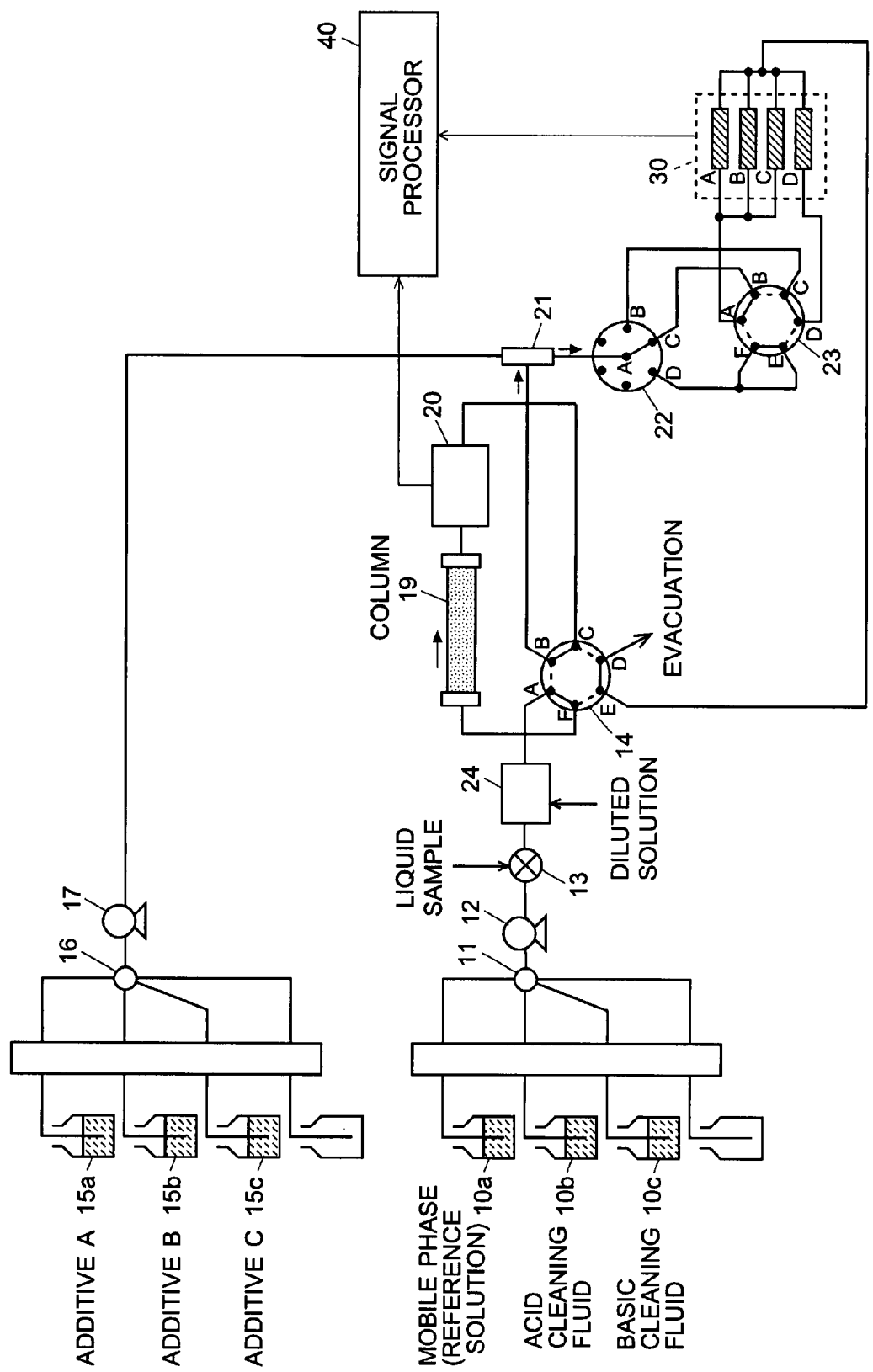
FIG. 7 is a schematic diagram showing the passages of the taste analyzing apparatus according to further another embodiment of the present invention.

It is also possible to insert an auto-diluter 24, as a diluter in accordance with an embodiment of the present invention, between the autosampler 13 and port A of the first 6-port-2-position valve 14 as shown in FIG. 7. In this mode, it is possible to easily perform an evaluation equivalent to the Taste Dilution Analysis by decreasing the concentration of the liquid sample injected into the mobile phase by the autosampler 13 in steps by the auto-diluter 24, and performing the analyses as described earlier in each of the steps. Moreover, by using an autosampler having an auto-diluting function, such as Autosampler SIL-10AF for High Performance Liquid Chromatograph by Shimadzu Corporation, the autosampler 13 and the auto-diluter 24 can be integrated. The auto-diluter 24 can be inserted to any flow passage other than that shown in FIG. 7. Also the blending means 21 can have a diluting function by blending a dilute solution, which is the same as the mobile phase, with the sample, in place of blending an additive with the sample.

Generally, since the mobile phase keeps flowing after the sample components are introduced into the taste detector 30, the sample components attached to lipid/polymer membranes of each taste sensor are washed away by the mobile phase, and the levels of the detection signals return to the levels before changing. If the concentration of the sample component is high, however, the sample component may remain firmly in the lipid/polymer membranes and therefore the levels of the detection signals do not return quickly. In such cases, the taste analyzing apparatus in accordance with an embodiment of the present invention can cleanse the lipid/polymer membranes of each taste sensor with cleaning fluid. When cleansing, it is preferable to use both acid cleaning fluid and basic cleaning fluid to suit the nature of the lipid/polymer membranes. Specifically, it is preferable to use acid cleaning fluid such as 30% ethanol+100 mM HCl to a lipid/polymer membrane having minus behavior, and use basic cleaning fluid such as 30% ethanol+100 mM HCl+10 mM KOH to a lipid/polymer membrane having plus behavior.

Since the flow passages in accordance with an embodiment of the present invention are configured with plural valves, it is possible to prevent conflicting cleaning fluids from getting mixed. When cleansing taste sensors A, B, and C which have minus behaviors, acid cleaning fluid is selected by the first switching valve 11, the 7-port-6-position valve 22 is set to the connection state as shown in FIG. 1, and the second 6-port-2-position valve 23 is set to the connection state as shown by solid lines in FIG. 1. The acid cleaning fluid sent by the first liquid sending pump 12 is introduced into the taste detector 30, and then each surface of the membranes of each taste sensor is cleansed. After cleansing sufficiently, the first switching valve 11 is switched to select the mobile phase, and the cleaning fluid in the flowing passages is replaced with the mobile phase.

On the other hand, when cleansing taste sensor D which has plus behaviors, basic cleaning fluid is selected by the first switching valve 11, ports A and B of the 7-port-6-position valve 22 are connected, and the second 6-port-2-position valve 23 is set to the connection state as shown by solid lines in FIG. 1. The basic cleaning fluid sent by the first liquid sending pump 12 is introduced into the taste detector 30, and each surface of the membranes of each taste sensor is cleansed. After cleansing sufficiently, the first switching valve 11 is switched to select the mobile phase, and the cleaning fluid in the flowing passages is replaced with the mobile phase. It is possible to replace all the cleaning fluids with the mobile phase in the flowing passage in the following way: ports A and D of the 7-port-6-position valve 22 are connected, and the second 6-port-2-position valve 23 is set to the connection state as shown by solid lines in FIG. 1. Then the mobile phase is sent through all the taste sensors A through D.

Although the taste detector 30 is used for determining tastes of each of the sample components as well as for determining the overall taste of the whole sample in the embodiment described above, it is possible, as a matter of course, to use separate taste detectors. However, taste sensors have relatively large inter-individual variability in general. Therefore, when relating the determining result of the whole sample to that of each sample component regarding the same sample, it is better to perform an analysis using detecting signals detected by the same taste sensor to heighten the accuracy of the analysis result.

(Second Embodiment)

Figure 6:
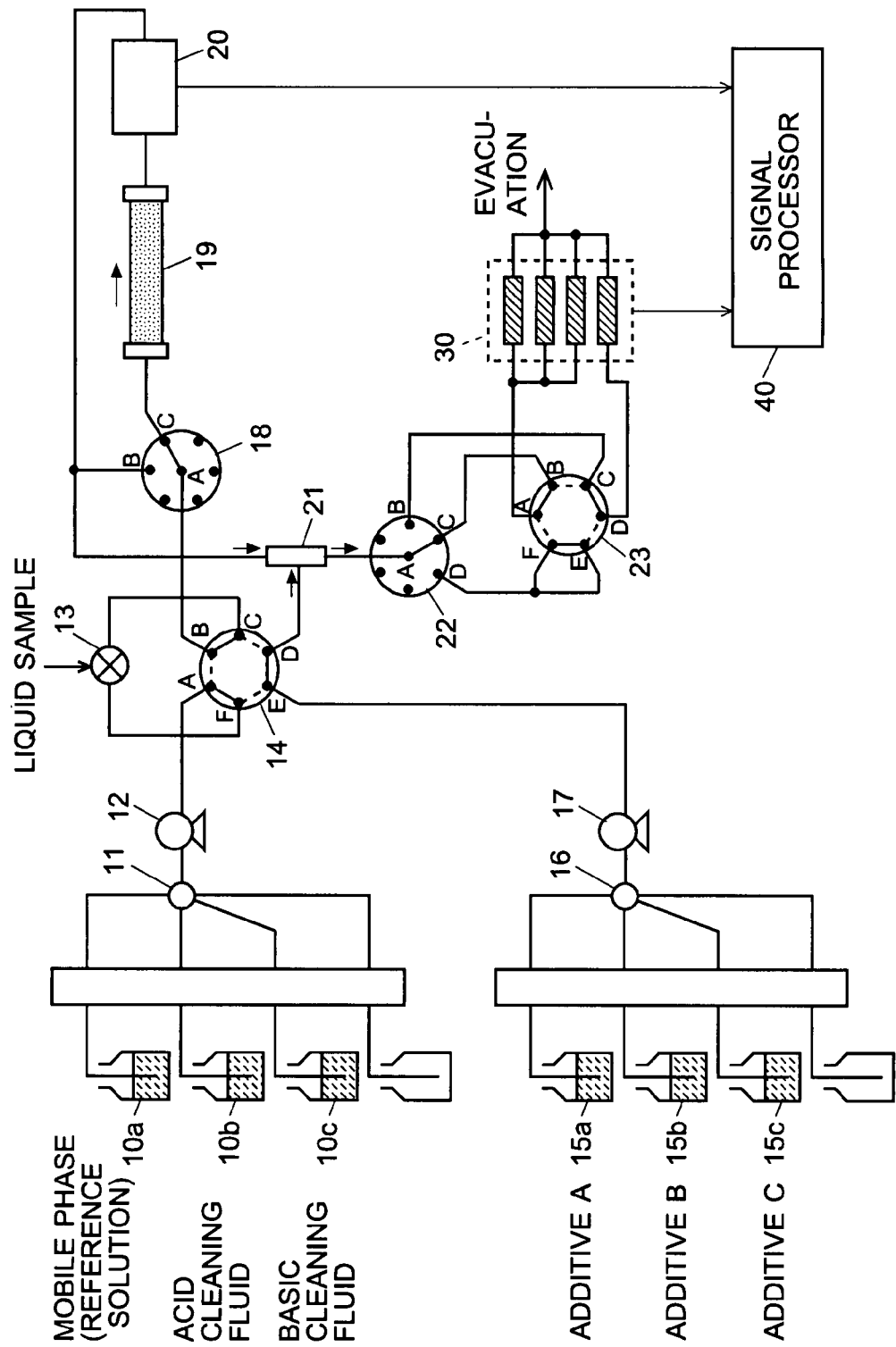
FIG. 6 is a schematic diagram showing the passages of the taste analyzing apparatus according to another embodiment of the present invention.

FIG. 6 is a schematic diagram showing the passages of the taste analyzing apparatus according to another (the second) embodiment of the present invention. In FIG. 6, like elements are denoted by like numerals as in FIG. 1. In this embodiment, unlike in the first embodiment, a liquid sample is evacuated directly after flowing thorough the taste detector 30. Therefore, it is not possible to determine the taste of the whole sample and determine the taste of each sample component at the same time in one analysis. Instead, since either a liquid sample not separated into components or an eluted liquid containing sample components which are separated into components by the column 19 can be sent to the taste detector 30 by switching the 7-port-6-position valve 18, it is possible to perform the same analysis as in the first embodiment by performing two analyses.

It should be noted that the embodiments described thus far are mere examples, which can be changed, modified or expanded within the spirit of the present invention.

For example, although in the embodiment described thus far, sample components which are separated by a column of a liquid chromatograph are introduced directly to the taste detector, it is possible to fractionate various sample components separated by a column into different containers by a fraction collector, introduce in series an eluted liquid containing the fractionated sample components to a taste detector. Consequently, signals from the taste sensors corresponding to each sample component are obtained.

Additionally, although a UV detector is used as a detector for identifying each sample component in the embodiment described thus far, other types of detectors such as a mass spectrometer can be used for improving the identification accuracy. Since a mass spectrometer consumes a sample, it is preferable to take a small amount of the eluted liquid from the column by a splitter and introduce it into the mass spectrometer. The remaining portion of the divided eluted liquid is introduced into the taste detector.

What is claimed is:

1. A taste analyzing apparatus for analyzing tastes which a liquid sample has, comprising:
   a) a component separator for temporally separating components contained in a liquid sample to be analyzed;
   b) a component detector located after the component separator for detecting the temporally separated components;
   c) a first taste detector including a plurality of taste sensors, each of which has a different responsive property, for detecting the components in the liquid sample separated by the component separator in temporal course;
   d) a signal processor for obtaining information on tastes corresponding to each component of the sample by processing detection signals obtained by the component detector and the first taste detector in order to determine not an overall taste of the sample but each taste of various components contained in the sample;
   e) a second taste detector including a plurality of taste sensors, each of the taste sensors having a different responsive property, for detecting tastes of the liquid sample before being separated into components by the component separator, wherein the first taste detector and the second taste detector are one same taste detector; and
   f) a passage switcher for selectively supplying the liquid sample before being separated into components by the component separator to the second taste detector, and supplying a liquid eluted from the component separator to the first taste detector.

2. The taste analyzing apparatus of claim 1, wherein the component separator is a separation column of a liquid chromatograph.

3. The taste analyzing apparatus of claim 1, further comprising an additive blender for selectively blending an additive into the sample after being separated into components by the component separator, wherein the sample separated into components by the component separator, each of the components having been blended with the additive, is detected by the first taste detector.

4. The taste analyzing apparatus of claim 1, further comprising an additive blender for selectively blending an additive into the sample before being separated into components by the component separator, wherein the sample being blended with the additive and not having been separated into components is detected by the second taste detector.

5. The taste analyzing apparatus of claim 1, further comprising an additive blender for selectively blending an additive into the sample before being separated into components by the component separator and the sample after being separated into components, wherein the sample being blended with the additive and not having been separated into components is detected by the second taste detector and the sample separated into components by the component separator, each of the components being blended with the additive, is detected by the first taste detector.

6. The taste analyzing apparatus of claim 1, further comprising a diluter for diluting the liquid sample, wherein the liquid sample properly diluted by the diluter is separated into components by the component separator and then is detected by the first taste detector.

7. The taste analyzing apparatus of claim 1, further comprising a diluter for diluting the liquid sample before being separated into components by the component separator, wherein the liquid sample properly diluted by the diluter and not having been separated into components is detected by the second taste detector.

8. The taste analyzing apparatus of claim 1, further comprising a diluter for diluting the liquid sample, wherein the liquid sample properly diluted by the diluter is detected by the second taste detector before separated into components and is detected by the first taste detector after separated into components by the component separator.

* * * * *